US011118160B2

United States Patent
Wan et al.

(10) Patent No.: US 11,118,160 B2
(45) Date of Patent: Sep. 14, 2021

(54) PROBIOTIC COMPOSITION FOR ENHANCING AN INSECTS RESISTANCE TO A PESTICIDE

(71) Applicant: The Regents of the University of California, Oakland, CA (US)

(72) Inventors: Kenneth H. Wan, El Cerrito, CA (US); James B. Brown, El Sobrante, CA (US); Susan E. Celniker, Lafayette, CA (US)

(73) Assignee: The Regents of the University of California, Oakland, CA (US)

( * ) Notice: Subject to any disclaimer, the term of this patent is extended or adjusted under 35 U.S.C. 154(b) by 181 days.

(21) Appl. No.: 16/183,529

(22) Filed: Nov. 7, 2018

(65) Prior Publication Data

US 2019/0177807 A1 Jun. 13, 2019

Related U.S. Application Data

(60) Provisional application No. 62/582,807, filed on Nov. 7, 2017.

(51) Int. Cl.
| | |
|---|---|
| *A01K 53/00* | (2006.01) |
| *C12N 1/20* | (2006.01) |
| *A23K 10/18* | (2016.01) |
| *A23K 50/90* | (2016.01) |
| *A61K 35/741* | (2015.01) |
| *A61P 1/14* | (2006.01) |
| *A61K 9/00* | (2006.01) |
| *A23K 10/33* | (2016.01) |
| *A23K 20/163* | (2016.01) |
| *C12R 1/02* | (2006.01) |

(52) U.S. Cl.
CPC .............. *C12N 1/205* (2021.05); *A01K 53/00* (2013.01); *A23K 10/18* (2016.05); *A23K 10/33* (2016.05); *A23K 20/163* (2016.05); *A23K 50/90* (2016.05); *A61K 9/0056* (2013.01); *A61K 35/741* (2013.01); *A61P 1/14* (2018.01); *A01K 2227/706* (2013.01); *C12R 2001/02* (2021.05)

(58) Field of Classification Search
CPC combination set(s) only.
See application file for complete search history.

(56) References Cited

PUBLICATIONS

Evans, J. et al J. Econ. Entomol. 2004 vol 97, pp. 752-756.*
Broderick NA, Lemaitre B. 2012. Gut-associated microbes of *Drosophila melanogaster*. Gut Microbes 3:307-21.
Newell PD, Douglas AE 2014. Interspecies interactions determine the impact of the gut microbiota on nutrient allocation in *Drosophila melanogaster*. Appl Environ Microbiol 80:788-96.
Newell PD, Chaston JM, Wang Y, Winans NJ, Sannino DR, Wong AC, Dobson AJ, Kagle J, Douglas AE. 2014. In vivo function and comparative genomic analyses of the *Drosophila* gut microbiota identify candidate symbiosis factors. Front Microbiol 5:576.
Yu Z, Morrison M. 2004. Comparisons of different hypervariable regions of rrs genes for use in fingerprinting of microbial communities by PCR-denaturing gradient gel electrophoresis. Appl Environ Microbiol 70:4800-6.
Slatko BE, Kieleczawa J, Ju J, Gardner AF, Hendrickson CL, Ausubel FM. 2011. "First generation" automated DNA sequencing technology. Curr Protoc Mol Biol Chapter 7:Unit7 2.
Wilson K. 2001. Preparation of genomic DNA from bacteria. Curr Protoc Mol Biol Chapter 2:Unit 2 4.
Korlach J, Bjornson KP, Chaudhuri BP, Cicero RL, Flusberg BA, Gray JJ, Holden D, Saxena R, Wegener J, Turner SW. 2010. Real-time DNA sequencing from single polymerase molecules. Methods Enzymol 472:431-55.
Chin CS, Alexander DH, Marks P, Klammer AA, Drake J, Heiner C, Clum A, Copeland A, Huddleston J, Eichler EE, Turner SW, Korlach J. 2013. Nonhybrid, finished microbial genome assemblies from long-read SMRT sequencing data. Nat Methods 10:563-9.
Koren S, Harhay GP, Smith TP, Bono JL, Harhay DM, McVey SD, Radune D, Bergman NH, Phillippy AM. 2013. Reducing assembly complexity of microbial genomes with single-molecule sequencing. Genome Biol 14:R101.
Chaisson MJ, Tesler G. 2012. Mapping single molecule sequencing reads using basic local alignment with successive refinement (BLASR): application and theory. BMC Bioinformatics 13:238.
Overbeek R, Olson R, Pusch GD, Olsen GJ, Davis JJ, Disz T, Edwards RA, Gerdes S, Parrello B, Shukla M, Vonstein V, Wattam AR, Xia F, Stevens R. 2014. The Seed and the Rapid Annotation of microbial genomes using Subsystems Technology (RAST). Nucleic Acids Res 42:D206-14.
Tatusova T, DiCuccio M, Badretdin A, Chetvemin V, Ciufo S, Li W 2013. Prokaryotic Genome Annotation Pipeline. In (ed), The NCBI Handbook [Internet]. National Center for Biotechnology Information (US), Bethesda (MD). Website for: ncbi.nlm.nih.gov/books/NBK174280/.
Zink SD, Pedersen L, Cianciotto NP, Abu-Kwaik Y. 2002. The Dot/Icm type IV secretion system of Legionella pneumophila is essential for the induction of apoptosis in human macrophages. Infect Immun 70:1657-63.

(Continued)

*Primary Examiner* — Heidi Reese (74) *Attorney, Agent, or Firm* — Robin C. Chiang; Lawrence Berkeley National Laboratory (57) ABSTRACT

The present invention provides for a probiotic composition for enhancing a subject's, such as an insect's, resistance to a pesticide comprising: (a) a microorganism capable of expressing one or more enzymes for metabolizing the pesticide, and (b) at least one feed ingredient for a subject. The present invention also provides for a method for enhancing a subject's, such as an insect's, resistance to a pesticide comprising administering to a subject the probiotic composition.

18 Claims, 5 Drawing Sheets

(56) References Cited

PUBLICATIONS

Luo C, Rodriguez RL, Konstantinidis KT. 2013. A users guide to quantitative and comparative analysis of metagenomic datasets. Methods Enzymol 531:525-47.

Ndoye B, Cleenwerck I, Engelbeen K, Dubois-Dauphin R, Guiro AT, Van Trappen S, Willems A, Thonart P. 2007. *Acetobacter senegalensis* sp. nov., a thermotolerant acetic acid bacterium isolated in Senegal (sub-Saharan Africa) from mango fruit (*Mangifera indica* L.). Int J Syst Evol Microbiol 57:1576-81.

Palmer, C., et al., Development of the human infant intestinal microbiota. PLoS biology, 2007. 5(7): p. e177.

Koenig, J.E., et al., Succession of microbial consortia in the developing infant gut microbiome. Proceedings of the National Academy of Sciences of the United States of America, 2011. 108 Suppl 1: p. 4578-4585.

Dominguez-Bello, M.G., et al., Delivery mode shapes the acquisition and structure of the initial microbiota across multiple body habitats in newborns. Proceedings of the National Academy of Sciences of the United States of America, 2010. 107(26): p. 11971-11975.

Turnbaugh, P.J. et al., Diet-induced obesity is linked to marked but reversible alterations in the mouse distal gut microbiome. Cell host & microbe, 2008. 3(4): p. 213-223.

Turnbaugh, P.J., et al., An obesity-associated gut microbiome with increased capacity for energy harvest. Nature, 2006. 444(7122): p. 1027-1031.

Ley, R.E., et al., Microbial ecology: human gut microbes associated with obesity. Nature, 2006. 444(7122): p. 1022-1023.

Muegge, B.D., et al., Diet drives convergence in gut microbiome functions across mammalian phylogeny and within humans. Science, 2011. 332(6032): p. 970-974.

Wu G.D., et al., Linking long-term dietary patterns with gut microbial enterotypes. Science, 2011. 334(6052): p. 105-108.

Diaz Heijtz, R., et al., Normal gut microbiota modulates brain development and behavior. Proceedings of the National Academy of Sciences of the United States of America, 2011. 108(7): p. 3047-3052.

Yoshimoto, S., et al., Obesity-induced gut microbial metabolite promotes liver cancer through senescence secretome. Nature, 2013. 499(7456): p. 97-101.

Caporaso, J.G., et al., Ultra-high-throughput microbial community analysis on the Illumina HiSeq and MiSeq platforms. The ISME journal, 2012. 6(8): p. 1621-1624.

Derrien, T., et al., The GENCODE v7 catalog of human long noncoding RNAs: analysis of their gene structure, evolution, and expression. Genome research, 2012. 22(9): p. 1775-1789.

\* cited by examiner

PROBIOTIC COMPOSITION FOR ENHANCING AN INSECTS RESISTANCE TO A PESTICIDE

CROSS-REFERENCE TO RELATED APPLICATIONS

This application claims priority to U.S. Provisional Patent Application Ser. No. 62/582,807, filed Nov. 7, 2017, which is incorporated by reference in its entirety.

STATEMENT OF GOVERNMENTAL SUPPORT

The invention was made with government support under Contract Nos. DE-AC02-05CH11231 awarded by the U.S. Department of Energy. The government has certain rights in the invention.

FIELD OF THE INVENTION

The present invention is in the field of probiotics.

BACKGROUND OF THE INVENTION

Exposures to a wide variety of chemicals can occur through non-targeted effects after leaching into water and food supplies. Of the >60,000 compounds industrial compounds, fewer than 7% have been toxicologically characterized in any system. Public health risks include increased carcinogenesis, immunodeficiency, lower cognitive performance and other behavioral deficits. Early life (in utero to puberty) is likely to be a particularly sensitive window-of-susceptibility for long-term health risk associated with pesticide exposure, since (1) internal organs including the brain are still developing, (2) when corrected for body weight, infants and children consume more food and water in comparison to adults and thus may be exposed to higher pesticide doses, and (3) exploratory behavior in infants and children increases exposure to commonly used pesticides in homes and yards. It is becoming increasingly apparent that the microbiome plays an important role in human and animal health. Several recent studies have demonstrated that obesity and diet influence the composition of the gut microbiome. Increasing evidence suggests an interaction between the gut microbiota, the gut and other organ systems, including the brain and liver. However, the effects of chemical exposures on the microbiome, and in turn animal physiology and viability, are poorly understood.

SUMMARY OF THE INVENTION

The present invention provides for a probiotic composition for enhancing a subject's, such as an insect's, resistance to a pesticide comprising: (a) a microorganism capable of expressing one or more enzymes for metabolizing the pesticide, and (b) at least one feed ingredient for an insect.

In some embodiments, the pesticide is an herbicide. In some embodiments, the herbicide is atrazine, glyphosate (Roundup®), bromacil, or paraquat. In some embodiments, the pesticide is cadmium chloride ($CdCl_2$), ethoprophos, or ziram.

In some embodiment, when the pesticide is atrazine, the one or more enzymes are atrazine chlorohydrolase (AtzA, encoded by the atzA gene), hydroxyatrazine ethylaminohydrolase (AtzB, encoded by the atzB gene), and/or N-isopropylammelid isopropylaminohydrolase (AtzC, encoded by the atzC gene).

In some embodiment, when the atrazine chlorohydrolase is an *Acetobacter* species, such as *Acetobacter tropicalis* or *Acetobacter pomorum*, atrazine chlorohydrolase. In some embodiment, when the hydroxyatrazine ethylaminohydrolase is an *Acetobacter* species, such as *Acetobacter tropicalis* or *Acetobacter pomorum*, hydroxyatrazine ethylaminohydrolase. In some embodiment, when the N-isopropylammelid isopropylaminohydrolase is an Acetobacter species, such as *Acetobacter tropicalis* or *Acetobacter pomorum*, N-isopropylammelid isopropylaminohydrolase.

In some embodiments, the microorganism is an *Acetobacter* species. In some embodiments, the *Acetobacter species* is *Acetobacter tropicalis* or *Acetobacter pomorum*. In some embodiments, the microorganism is a genetically modified microorganism modified to be capable of expressing the one or more enzymes for metabolizing the pesticide. In some embodiments, the microorganism is heterologous to the one or more enzymes. In some embodiments, the microorganism is a genetically modified microorganism modified to be capable of expressing the one or more enzymes for metabolizing the pesticide, wherein the one or more enzymes are native to the microorganism, and the genetically modified microorganism expresses the one or more enzymes at a higher level than in the microorganism if not unmodified. In some embodiments, the microorganism comprises one or more nucleic acids encoding the one or more enzymes operatively linked to one or more promoters such that the microorganism is capable of expressing the one or more enzymes. In some embodiments, the nucleic acid is a recombinant polynucleotide. In some embodiments, the nucleic acid is stably maintained in the microorganism, such as in an expression vectors or vectors, or stably integrated into a chromosome of the microorganism.

In some embodiments, the microorganism is naturally found in the gut of the subject. In some embodiments, the microorganism is non-pathogenic to the subject. In some embodiments, the microorganism is a *Lactobacillus* species, such as *Lactobacillus brevis* or *Lactobacillus plantarum*; a *Bacillus* species, such as *Bacillus kochii* or *Bacillus flexus*; an *Enterococcus* species, such as *Enterococcus durans*; or, a *Paenibacillus* species, such as *Paenibacillus taichungensis*.

In some embodiments, the composition comprises an effective amount of the microorganism. In some embodiments, the composition comprises about $1\times10^3$ CFU/g feed ingredient, $1\times10^4$ CFU/g feed ingredient, $1\times10^5$ CFU/g feed ingredient, $1\times10^6$ CFU/g feed ingredient, $1\times10^7$ CFU/g feed ingredient, $1\times10^8$ CFU/g feed ingredient, $1\times10^9$ CFU/g, $1\times10^{10}$ CFU/g feed ingredient, or any range between any two values described herein, of the microorganism. In some embodiments, the effective amount of the microorganism is about $1\times10^3$ CFU/g feed ingredient to about $1\times10^{10}$ CFU/g feed ingredient. In some embodiments, the effective amount of the microorganism is about $1\times10^3$ CFU/g feed ingredient, $1\times10^4$ CFU/g feed ingredient, $1\times10^5$ CFU/g feed ingredient, $1\times10^6$ CFU/g feed ingredient, $1\times10^7$ CFU/g feed ingredient, $1\times10^8$ CFU/g feed ingredient, $1\times10^9$ CFU/g, $1\times10^{10}$ CFU/g feed ingredient, or any range between any two values described herein.

In some embodiments, the subject is an insect. In some embodiments, the insect is an insect that has economical value, such as an insect that is a producer of a commercially valuable product, beneficial to agricultural crops, or a predator of a pest. In some embodiments, the insect is a bee. In some embodiments, the bee is a honey bee. In some embodiments, the honey bee of the species *Apis florea, Apis andreniformis, Apis mellifera, Apis cerana, Apis dorsata*, or

*Apis koschenikovi.* In some embodiments, the insect is a *Drosophila,* such as a *Drosophilia melanogaster,* or a mosquito.

In some embodiments, the feed ingredient is white sugar, raw sugar, brown sugar, molasses, waste sugar, honey, syrup, or a mixture thereof. In some embodiments, the composition lacks salt and/or starch.

The present invention provides for a method for enhancing a subject's, such as an insect's, resistance to a pesticide comprising administering to a subject the probiotic composition of the present invention, or any microorganism described herein.

In some embodiments, the administering step comprises placing the composition in a device configured to attract the insect. In some embodiments, the device comprises a flower. In some embodiments, the device comprises a plant comprising the flower. In some embodiments, the flower is of one species selected form the group consisting of: American Basswood, Southern Magnolia, Sourwood, Redbud, Crabapple, Locust, Serviceberry, Tulip Tree, Catmint, Calendula, Bee balm, Sedum, Lavender, Borage, Foxglove, Crocus, Anise hyssop, Heliotrope, Pansy, Pussy willow, Siberian squill, Snowdrops, Peony, Milkweed, Phlox, Zinnia, Marigold, Goldenrod, Chive, Liatris, Mint, Sage, Nasturtium, Black-eyed Susans, Borage, Thyme, and Oregano. In some embodiments, the placing step comprises introducing the composition onto the flower, or into a region surrounded by the petals containing the stamen and carpel of the flower. In some embodiments, the introducing step comprising spraying the composition onto the flower or into the region of the flower.

In some embodiments, the method further comprises the step of mixing a microorganism capable of expressing one or more enzymes for metabolizing the pesticide, and at least one feed ingredient for a subject to produce the composition.

The present invention provides for a method of making the probiotic composition for enhancing a subject's, such as an insect's, resistance to a pesticide comprising: mixing a microorganism capable of expressing one or more enzymes for metabolizing the pesticide, and at least one feed ingredient for a subject to produce the probiotic composition of the present invention.

BRIEF DESCRIPTION OF THE DRAWINGS

The foregoing aspects and others will be readily appreciated by the skilled artisan from the following description of illustrative embodiments when read in conjunction with the accompanying drawings.

DETAILED DESCRIPTION OF THE INVENTION

Before the invention is described in detail, it is to be understood that, unless otherwise indicated, this invention is not limited to particular sequences, expression vectors, enzymes, host microorganisms, or processes, as such may vary. It is also to be understood that the terminology used herein is for purposes of describing particular embodiments only, and is not intended to be limiting.

In this specification and in the claims that follow, reference will be made to a number of terms that shall be defined to have the following meanings:

The terms "optional" or "optionally" as used herein mean that the subsequently described feature or structure may or may not be present, or that the subsequently described event or circumstance may or may not occur, and that the description includes instances where a particular feature or structure is present and instances where the feature or structure is absent, or instances where the event or circumstance occurs and instances where it does not.

As used in the specification and the appended claims, the singular forms "a," "an," and "the" include plural referents unless the context clearly dictates otherwise. Thus, for example, reference to an "expression vector" includes a single expression vector as well as a plurality of expression vectors, either the same (e.g., the same operon) or different; reference to "cell" includes a single cell as well as a plurality of cells; and the like.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

The term "about" refers to a value including 10% more than the stated value and 10% less than the stated value.

The term "heterologous" as used herein refers to a material, or nucleotide or amino acid sequence, that is found in or is linked to another material, or nucleotide or amino acid sequence, wherein the materials, or nucleotide or amino acid sequences, are foreign to each other (i.e., not found or linked together in nature).

The terms "expression vector" or "vector" refer to a compound and/or composition that transduces, transforms, or infects a host microorganism, thereby causing the cell to express nucleic acids and/or proteins other than those native to the cell, or in a manner not native to the cell. An "expression vector" contains a sequence of nucleic acids (ordinarily RNA or DNA) to be expressed by the host microorganism. Optionally, the expression vector also comprises materials to aid in achieving entry of the nucleic acid into the host microorganism, such as a virus, liposome, protein coating, or the like. The expression vectors contemplated for use in the present invention include those into which a nucleic acid sequence can be inserted, along with any preferred or required operational elements. Further, the expression vector must be one that can be transferred into a host microorganism and replicated therein. Particular expression vectors are plasmids, particularly those with restriction sites that have been well documented and that contain the operational elements preferred or required for transcription of the nucleic acid sequence. Such plasmids, as well as other expression vectors, are well known to those of ordinary skill in the art.

The term "operatively linked" refers to a functional relationship between two or more polynucleotide (e.g., DNA) segments. Typically, it refers to the functional relationship of a transcriptional regulatory sequence to a transcribed sequence. For example, a promoter or enhancer sequence is operably linked to a DNA or RNA sequence if it stimulates or modulates the transcription of the DNA or RNA sequence in an appropriate host cell or other expression system. Generally, promoter transcriptional regulatory sequences that are operably linked to a transcribed sequence are physically contiguous to the transcribed sequence, i.e., they are cis-acting. However, some transcriptional regulatory sequences, such as enhancers, need not be physically contiguous or located in close proximity to the coding sequences whose transcription they enhance.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference to disclose and describe the methods and/or materials in connection with which the publications are cited.

The genome of *Acetobacter tropicalis*, one of the most abundant species in the fly gut, includes a complete folate synthesis pathway. Further, in all eight species sequenced, complete plasmid and viral sequences are identified that expand the metabolic potential of these microorganisms. *Acetobacter tropicalis* has a complete set of enzymes required for atrazine metabolism on a single plasmid. GF flies are fully rescued and wild-type survival curves are restored by feeding flies an *A. tropicalis* culture prior to atrazine exposure sensitivity to pesticide could be rescued by feeding a bacteria. Candidate genes for pesticide metabolism are found on a plasmid carried by the bacteria.

It is to be understood that, while the invention has been described in conjunction with the preferred specific embodiments thereof, the foregoing description is intended to illustrate and not limit the scope of the invention. Other aspects, advantages, and modifications within the scope of the invention will be apparent to those skilled in the art to which the invention pertains.

All patents, patent applications, and publications mentioned herein are hereby incorporated by reference in their entireties.

The invention having been described, the following examples are offered to illustrate the subject invention by way of illustration, not by way of limitation.

EXAMPLE 1

Microbiome Adaptation in Response to Environmental Challenges

This example characterizes the role of the microbiome in adaptation to environmental challenges. The microbiome has been linked to brain health, liver function, bowel disease, and many other physiological and behavioral phenotypes in a growing number of studies. However, the response of the microbiome to chemical perturbations is poorly understood. Accidental human and animal herbicide exposures to agricultural chemicals remain a serious problem in the United States, which accounts for 32% of the total global pesticide market. The role of the microbiome in adaptation to chronic pesticide exposures at environmentally relevant doses is characterized. By using both invertebrate and mammalian models, the impact of the gut microbiome on host health is elucidated to generate an atlas of microbiome chemical interactions in an organism.

The immediate and long-term responses of the gut microbiome to the top ten most utilized herbicides in the United States are measured using the model organism *Drosophila melanogaster*. By utilizing both gnotobiotic and wild-type flies in these perturbations, effects specifically due to the microbiome are isolated. Based on the results of the fly model, compounds are tested in mice in pre-adolescent exposure scenarios and long-term effects. As in the fly, genomic and metabolomics techniques are used. Detailed, life course assays throughout 12-week span would provide an extensive map of the dynamic composition of mammalian gut microbiomes. Identification of microbiome chemical and genetic interactions are obtained by utilizing the collaborative cross mice and also specified microbial compositions. Pesticide-induced changes in behavior are correlated with changes in the microbiome, while controlling for genetic background.

Using Pacific Biosciences (PacBio) technology eight species are sequenced, and for six (*Acetobacter tropicalis, Lactobacillus brevis, Bacillus kochii, Enterococcus durans, Lactobacillus plantarum, Acetobacter pomorum*), a large core circular genome in a single gapless contig assembly is identified, while for two others (*Paenibacillus taichungensis, Bacillus flexus*) they are in three contigs. In the case of one species, this greatly improved assembly (the previous assembly was in hundreds of small contigs and revealed >1000 new genes and fundamentally new metabolic potentials. It has long been suspected that fruit flies synthesize folate (vitamin B12) from their microbiomes, since feeding antibiotics strongly reduces growth and survival on folate-free media. The genome of *Acetobacter tropicalis*, one of the most abundant species in the fly gut, includes a complete folate synthesis pathway. Further, in all eight species sequenced, we identified complete plasmid and viral sequences that expand the metabolic potential of these microorganisms.

*Acetobacter tropicalis* also has a complete set of enzymes required for metabolism of atrazine, a known pesticide. Gnotobiotic flies lacking this pathway are significantly more susceptible to toxicity from this pesticide than wild-type strains having the pathway. Axenic adult flies are generated and exposures are recapitulated. Germ free (GF) flies exposed die earlier than control flies with wild-type microbiomes. Further, GF flies are fully rescued and wild-type survival curves are restored by feeding flies the bacterial culture prior to exposure. Similar rescue experiments with other microbes are attempted, none of which are rescued.

The GF condition does not make flies uniformly more susceptible to toxic compounds, as the wild-type microbiome offers no protection against certain toxicity.

EXAMPLE 2

Complete Genome Sequence of *Acetobacter tropicalis* Oregon-R-modENCODE Strain BDGP1, an Acetic Acid Bacterium Found in the *Drosophila melanogaster* Gut

*Acetobacter tropicalis* Oregon-R-modENCODE strain BDGP1, is isolated from *Drosophila melanogaster* for functional host microbial interaction studies. The complete genome is comprised of a single chromosomal circle of 3,988,649 bp with a G+C content of 56% and a conjugative plasmid of 151,013 bp.

In *Drosophila*, *Acetobacter* are one of the major commensals of the gut microbiota and contribute to larval growth (reviewed in (1)). Furthermore, mono-colonization of *Drosophila* with *Acetobacter* species significantly reduced host development (2). The first draft sequence of *A. tropicalis* from *Drosophila*, published in 2014, consisted of 129 contigs (3). The complete genome consists of a single chromosome and a conjugative plasmid.

*A. tropicalis* Oregon-R-modENCODE strain BDGP1 is isolated from a fecal swab. Bacteria are streaked onto Nutrient Broth Agar (BD Cat. No. 213000) plates, single colonies are amplified in culture and an aliquot used for 16S V1 and V4 PCR (4) and sequence identification (reviewed in (5)). DNA for sequencing is isolated (6) and whole-genome DNA sequencing is performed by the National Center for Genome Resources (NCGR), Santa Fe N. Mex. using Pacific Biosciences (PacBio) long reads on the RS II instrument (7). A single molecule real-time (SMRT) cell library is constructed with 5-10 µg DNA using the PacBio 20-kbps protocol. The library is sequenced using P6 polymerase and C4 chemistry with 6 hr movie times. Sequencing yields a total of 78,825 reads with filtered mean read length of 17,469 bps, totaling 1,377,023,046 bps (>200 and >400 fold coverage; chromosome and plasmid, respectively). A de novo assembly is constructed using the hierarchical genome assembly process (HGAP2) protocol from SMRT Analysis v2.0 (8-10). The final contigs are manually trimmed and reviewed to produce a single circular chromosome and a single plasmid. Annotations of protein-encoding open reading frames (ORFs) and ncRNAs are predicted using the RAST tool (11) and also predicted using the GenBank annotation pipeline (12).

The chromosomal genome annotation predicts 3,645 genes total; 3,446 protein-coding genes, 77 RNA genes including five rRNA operons, 58 tRNA genes, one tmRNA, three ncRNAs and 122 pseudo genes. Of the 3,446 protein coding genes 82 are contained within two candidate prophages (29 kb, 31 genes and 39 kb, 51 genes) characterized by genes encoding tailed phage morphogenetic, portal and terminase large subunit proteins and bounded by genes encoding phage lysin (lysozyme) and integrase. The candidate prophages are only 1.7% of the genome. Additionally, the genome contains a single plasmid pAtBDGP1A (151,013 bp) with a predicted G+C content of 52%. The plasmid contains 145 candidate protein-coding genes. Among them, genes essential for conjugation, TraA, TraG, TraW and TraY, plasmid replication RepA, RepB and replication protein C and likely members of a bacterial transport system TraI/DotC, DotG, DotH, IcmB/DotO and IcmL/DotI (reviewed in (13)). The plasmid also contains virulence proteins for arsenic resistance.

The sequence has significant similarity to Acetobacter senegalensis 108B, 97% identical by average nucleotide identity (ANI) (14) with 77% coverage of the genome. A. senegalensis originated from a spontaneous cocoa bean fermentation process (GenBank Accession Number LN606600.1)). Despite the sequence similarity, phenotypically the strain belongs to the *A. tropicalis* species based on its ability to grow on maltose and not grow on 10% ethanol nor on yeast extract supplemented with 30% D-glucose (15).

Nucleotide sequence accession numbers. The chromosome and plasmid sequences of *A. tropicalis* Oregon-R-modENCODE strain, BDGP1 are deposited in GenBank (accession numbers CP022699 (chromosome), CP022700 (pAtBDGP1A)).

REFERENCES CITED

1. Broderick N A, Lemaitre B. 2012. Gut-associated microbes of *Drosophila melanogaster*. Gut Microbes 3:307-21.
2. Newell P D, Douglas A E. 2014. Interspecies interactions determine the impact of the gut microbiota on nutrient allocation in *Drosophila melanogaster*. Appl Environ Microbiol 80:788-96.
3. Newell P D, Chaston J M, Wang Y, Winans N J, Sannino D R, Wong A C, Dobson A J, Kagle J, Douglas A E. 2014. In vivo function and comparative genomic analyses of the *Drosophila* gut microbiota identify candidate symbiosis factors. Front Microbiol 5:576.
4. Yu Z, Morrison M. 2004. Comparisons of different hypervariable regions of rrs genes for use in fingerprinting of microbial communities by PCR-denaturing gradient gel electrophoresis. Appl Environ Microbiol 70:4800-6.
5. Slatko B E, Kieleczawa J, Ju J, Gardner A F, Hendrickson C L, Ausubel F M. 2011. "First generation" automated DNA sequencing technology. Curr Protoc Mol Biol Chapter 7:Unit7 2.
6. Wilson K. 2001. Preparation of genomic DNA from bacteria. Curr Protoc Mol Biol Chapter 2:Unit 2 4.
7. Korlach J, Bjornson K P, Chaudhuri B P, Cicero R L, Flusberg B A, Gray J J, Holden D, Saxena R, Wegener J, Turner S W. 2010. Real-time DNA sequencing from single polymerase molecules. Methods Enzymol 472: 431-55.
8. Chin C S, Alexander D H, Marks P, Klammer A A, Drake J, Heiner C, Clum A, Copeland A, Huddleston J, Eichler E E, Turner S W, Korlach J. 2013. Nonhybrid, finished microbial genome assemblies from long-read SMRT sequencing data. Nat Methods 10:563-9.
9. Koren S, Harhay G P, Smith T P, Bono J L, Harhay D M, McVey S D, Radune D, Bergman N H, Phillippy A M. 2013. Reducing assembly complexity of microbial genomes with single-molecule sequencing. Genome Biol 14:R101.
10. Chaisson M J, Tesler G. 2012. Mapping single molecule sequencing reads using basic local alignment with successive refinement (BLASR): application and theory. BMC Bioinformatics 13:238.
11. Overbeek R, Olson R, Pusch G D, Olsen G J, Davis J J, Disz T, Edwards R A, Gerdes S, Parrello B, Shukla M, Vonstein V, Wattam A R, Xia F, Stevens R. 2014. The SEED and the Rapid Annotation of microbial genomes using Subsystems Technology (RAST). Nucleic Acids Res 42:D206-14.

12. Tatusova T, DiCuccio M, Badretdin A, Chetvernin V, Ciufo S, Li W. 2013. Prokaryotic Genome Annotation Pipeline. In (ed), The NCBI Handbook [Internet]. National Center for Biotechnology Information (US), Bethesda (MD). Website for: ncbi.nlm.nih.gov/books/NBK174280/.
13. Zink S D, Pedersen L, Cianciotto N P, Abu-Kwaik Y. 2002. The Dot/Icm type IV secretion system of *Legionella pneumophila* is essential for the induction of apoptosis in human macrophages. Infect Immun 70:1657-63.
14. Luo C, Rodriguez R L, Konstantinidis K T. 2013. A user's guide to quantitative and comparative analysis of metagenomic datasets. Methods Enzymol 531:525-47.
15. Ndoye B, Cleenwerck I, Engelbeen K, Dubois-Dauphin R, Guiro A T, Van Trappen S, Willems A, Thonart P. 2007. *Acetobacter senegalensis* sp. nov., a thermotolerant acetic acid bacterium isolated in Senegal (sub-Saharan Africa) from mango fruit (*Mangifera indica* L.). Int J Syst Evol Microbiol 57:1576-81.

EXAMPLE 3

Exposures to a wide variety of chemicals can occur through non-targeted effects after leaching into water and food supplies. Of the >60,000 compounds industrial compounds, fewer than 7% have been toxicologically characterized in any system. Public health risks include increased carcinogenesis, immunodeficiency, lower cognitive performance and other behavioral deficits. Early life (in utero to puberty) is likely to be a particularly sensitive window-of-susceptibility for long-term health risk associated with pesticide exposure, since (1) internal organs including the brain [1-3] are still developing, (2) when corrected for body weight, infants and children consume more food and water in comparison to adults and thus may be exposed to higher pesticide doses, and (3) exploratory behavior in infants and children increases exposure to commonly used pesticides in homes and yards. It is becoming increasingly apparent that the microbiome plays an important role in human and animal health. Several recent studies have demonstrated that obesity [4-6] and diet [7, 8] influence the composition of the gut microbiome. Increasing evidence suggests an interaction between the gut microbiota, the gut and other organ systems, including the brain and liver [9, 10]. However, the effects of chemical exposures on the microbiome, and in turn animal physiology and viability, are poorly understood.

Environmental exposure to pesticides has an influence on the composition, organization and function of the gut microbiome, resulting in host phenotypes dependent on the age at the time of exposure, genetic background and dosage. This study described herein would elucidate the role of the gut microbiome in organismal responses to pesticide exposure, and serve as a model for future, high-throughput studies of the effects of environmental challenges on metazoans and microbiome-mediated adaptation.

Plan Summary

Exposures in fly models in medium throughput (~10 toxicants per year) are studied. The results of the fly studies contextualize and prioritize work in mouse. Initially, the effects of Paraquat on the mouse gut microbiome during a critical window of development is assessed in genetically diverse mouse strains. Furthermore whether alterations can be correlated with organ structure and function is determined focusing on the gut and behavior.

AIM 1 Screen 20 most commonly used agricultural pesticides in the United States. Determine which pesticides impact microbiome composition in adult flies, leveraging the viability of germ-free animals and rapid life cycle. Measure the immediate (2 hrs) and long-term (10 days) responses of the microbiome to exposure using methods described below.

1A) Characterize the wild-type adult gut microbiome: metagenomic and meta-transcriptomic sequencing. Design and use custom microarrays for the fly microbiome.

1B) In situ imaging of specific microbes in dissected wild-type fly guts to obtain physical maps of microbial-host interactions before and after exposure. This structural map will provide histological phenotypes, and be the first 3D characterization of an animal gut microbiome.

1C) 16S-seq and microarray of microbiome before and after perturbation to quantify all microbial species and their transcriptomes. For treatments with strong effects, sequence the fly gut transcriptome (RNA-seq) to determine gene networks and pathways affected by exposure.

1D) Automated behavioral screening in 2D population cages with social affinity, aggression, and mating behavioral quantitative phenotypes. These are ideal because they integrate many aspects of the perturbed animal system, and will allow one skilled in the art to identify subtle neurological phenotypes may be missed by other modalities.

AIM 2 Characterize the microbiome and host gut physiology of mice before, during and after pre-pubescent chronic chemical exposure. Monitor the impact of pesticides during in the pre-pubescent phase, a sensitive window-of-susceptibility for exposure effects. Priority exposures will be determined in the fly screen in Aim 1.

2A) Characterize the prepubescent and adult gut microbiome using unbiased metagenomic and metatranscriptomic sequencing to determine functional gene composition and expression of the cecal microbiome and design custom microarray.

2B) High-throughput 16S sequencing of the gut microbiome before and after chemical perturbation. The 16S method allows for fast, high-throughput determination of the gut microbiome composition.

2C) Investigate bacterial-host interactions by imaging specific bacteria in dissected guts at multiple time-points during and after exposure, RNA-seq of host gut transcriptome, monitoring of gut physiology, including local immune response and cell death.

2D) Metabolic profiling: to characterize specific members of the gut microbiome, the metabolites they produce and host fitness effects, profile gut and plasma metabolites.

2F) Behavioral screening including motor skills and anxiety tests.

AIM 3 Integrative Analysis to ascertain the effects of environmental challenges on the gut microbiome and associated phenotypes: quantitatively comparable maps of the dynamic gut microbiomes in flies and mice as they respond to chronic pesticide exposures.

3A) Assemble metagenomes and metatranscriptomes. Design custom microarrays for metatranscriptomic profiling.

3B) Quantify changes in microbial populations from 16S data

3C) Use in situ imaging data to produce the first 3D map of a metazoan microbiome.

3D) Identify microbiome-mediated phenotypes, using regression analysis of microbiome, behavior, host transcriptome, and dosage data.

Approach

*Drosophila* is used to establish the infrastructure for future high-throughput screening. The adult fly gut microbiome (GM) are comprehensively characterized at two time points after exposure to pesticides using metagenomic and metatranscriptomic sequencing. This information is utilized to select unbiased (insofar as this is possible) universal 16S primers, and to design custom GM microarrays that will reduce the cost of GM profiling >10-fold. In situ imaging is used to identify structural organization of the microbes in the gut. The application of environmental challenges in wild-type and gnotobiotic backgrounds, followed by behavioral screening enables one skilled in the art to identify GM-mediated effects on host fitness. To isolate microbiome-mediated effects on gut physiology, plasma metabolites and behavior, gnotobiotic capabilities to colonize germ-free animals (both flies and mice) are established with specified microbes, including communities isolated from exposed animals. Additionally, all host tissues, DNA, and RNA samples collected incidentally in this study are preserved at −80° C. for future sequencing to molecularly characterize the host-GM interactome. A more extensive description of this approach in mouse is described below, where the experimental design is more complex. Wherever possible, the fly and mouse models are "parallel", in that assays and measurement modalities are matched to optimize the informativeness of integrative analysis.

In mice, pre-pubescent exposure regimes are desirable for microbiome-environmental interaction studies that focus on host health. Key developmental pathways have already been executed, so profound physiological effects due to environmental challenges will not confound attempts to quantify the role of the microbiome in host health and adaptation. In addition, the organism is still maturing, so microbiome-mediated interference with, for example, host hormone signaling would produce overt phenotypes. Mice are exposed to real-world pesticide doses under the following scenarios: 1) placebo, 2) low dose (10-100 fold below the EPA estimated 'safe-dose'), 3) high dose (guided by the EPA estimated 'safe' reference dose).

Exposures is chronic, and hence spans pre-puberty and puberty. The microbiome is monitored using a combination of 'omics' approaches. The mouse cecal microbiome is characterized using metagenomic and metatranscriptomic sequencing over time, doses and host genetic backgrounds. The functional gene repertoire and their expression profiles are determined in relation to host fitness, behavior and health. DNA is extracted from fecal and cecal samples and the microbial composition is determined by targeted sequencing 16S rRNA genes by multiplexing 96 samples per sequencing reaction using bar-coded primers for a total of 15 lanes of high throughput sequencing on the Illumina MiSeq platform [11].

Gut measurements fly/mouse: Mapping of bacterial proteins in the gut, immunohistochemical analyses of gut epithelial integrity, proliferation, apoptosis, immune cell infiltration.

Metabolite profiling: Metabolites is quantified in 60 fecal water extracts and 60 blood plasma samples by FT/ICR mass spectrometry. This shotgun, non-targeted approach is used to determine a wide range of known (and unknown) metabolites. The resulting data is correlated with exposure, behavior and gut physiology. The data is screened for known neuroactive metabolites that are known signaling molecules.

Murine behavioral studies: Motor skills. Mice are tested for their ability to maintain themselves upright (i.e. motor coordination) on a rotating rod (rotarod test). Anxiety. A light/dark test is used to assess anxiety. Since rodents are subject to predation, their innate tendency is to avoid brightly lit areas. This task takes advantage of the natural conflict between fear of open and bright areas versus desire to explore novel environments.

Fly behavioral studies: A 2D cage design with CCD video and fly tracking software is utilized widely by the community (19270697). This techniques enables the automated quantification of social affinity, aggression, and mating behavioral phenotypes.

Integrative analysis. Statistical machine learning analyses are conducted to identify groups of genes and pathways associated with behavioral phenotypes, leveraging the defined GM controls. Joint analysis is also conducted with the Drosophila dataset to identify common GM responses, if any, between these vertebrate and invertebrate models.

Design of custom microarrays. The initial metagenomic and metatranscriptomic profiling of both mouse and fly systems are leveraged to design custom arrays, which lead to a 10-fold cost savings on metatranscriptomic profiling. Microarray designs are described [12].

Figure 1:
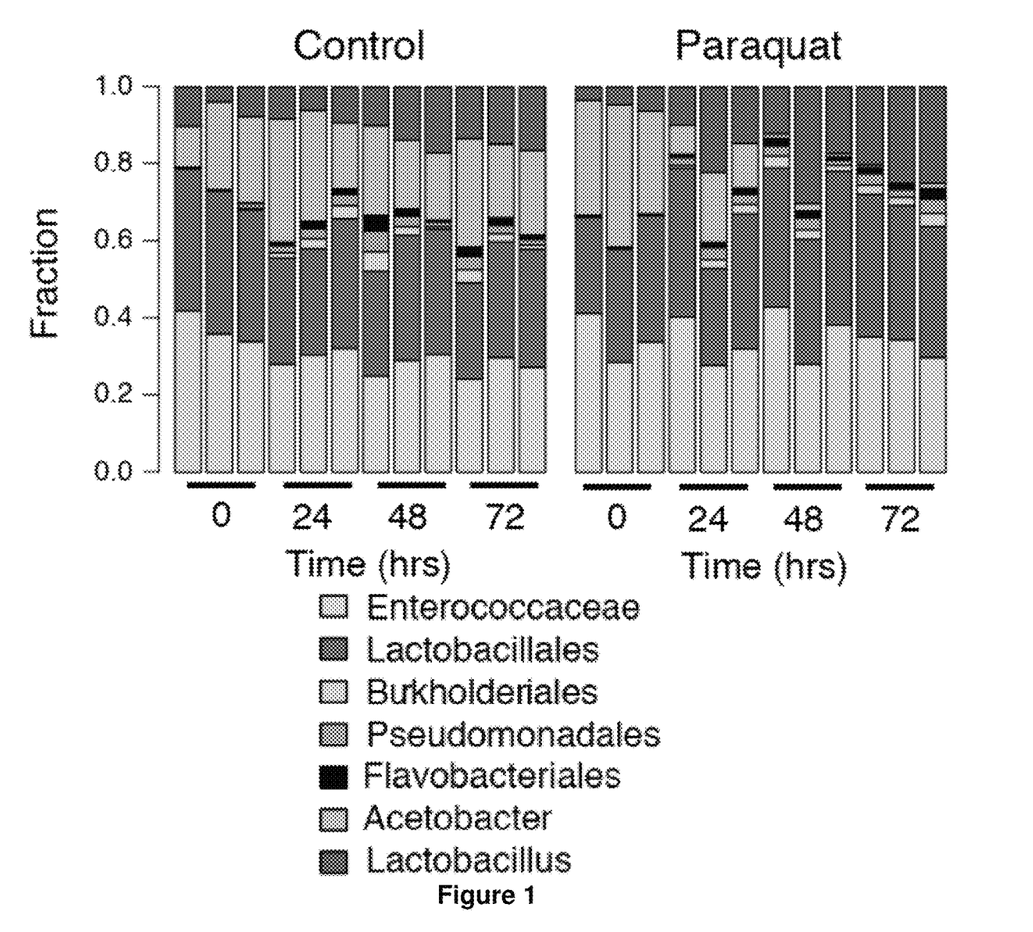
FIG. 1 shows the remodeling of the microbiome in response to exposure to paraquat. Paraquat and atrazine induce the collapse of Acetobacter in the insect gut. Atrazine is rapidly and completely metabolized in the host gut, yet it still induces a hyperactive phenotype.
Figure 2:
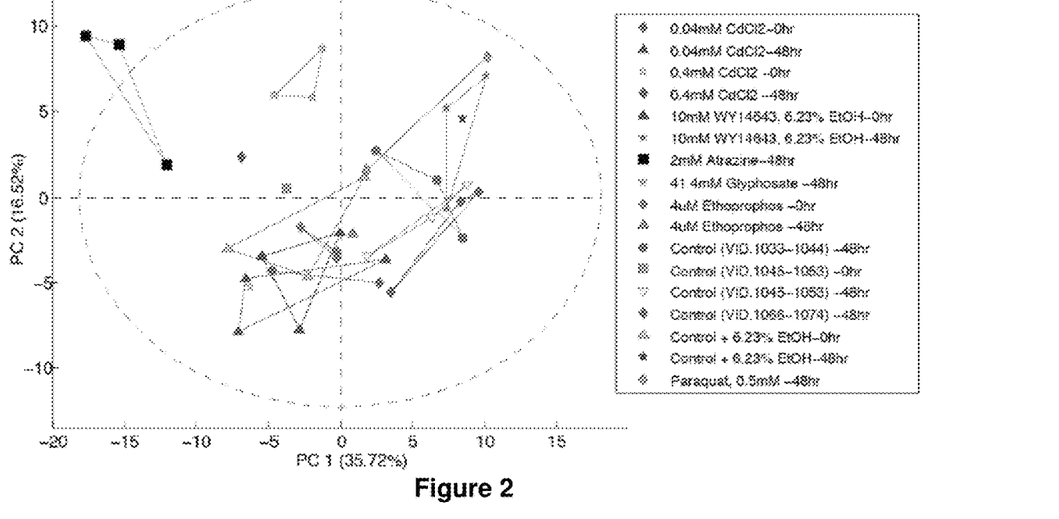
FIG. 2 shows the summary of results of fecal metabolomes.
Figure 3:
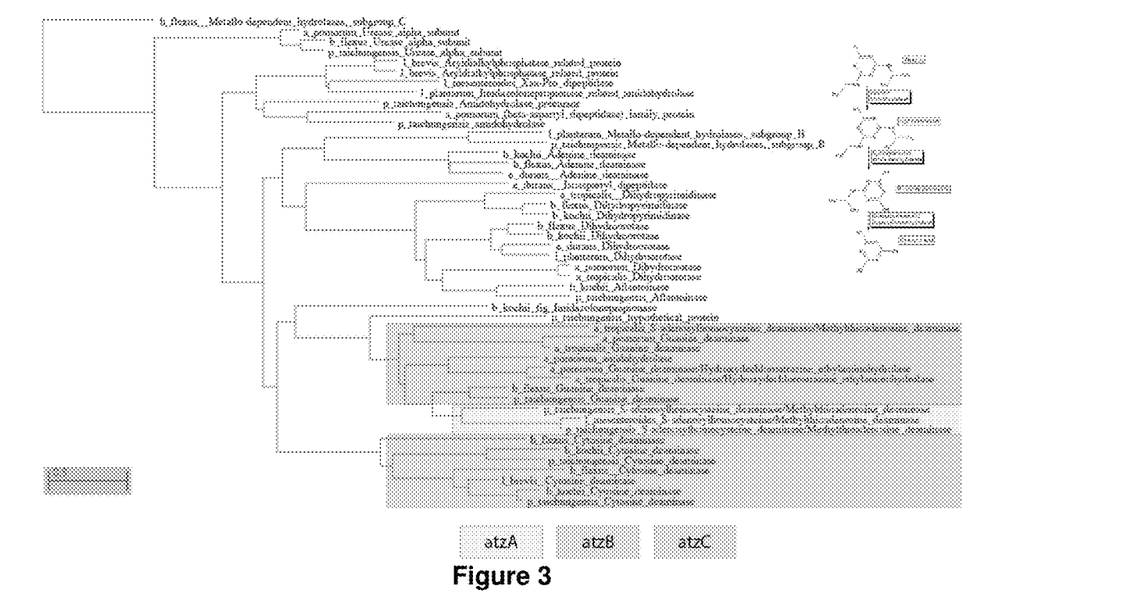
FIG. 3 shows the candidate atrazine metabolizing genes from sequenced fly gut microbes.
Figure 4:
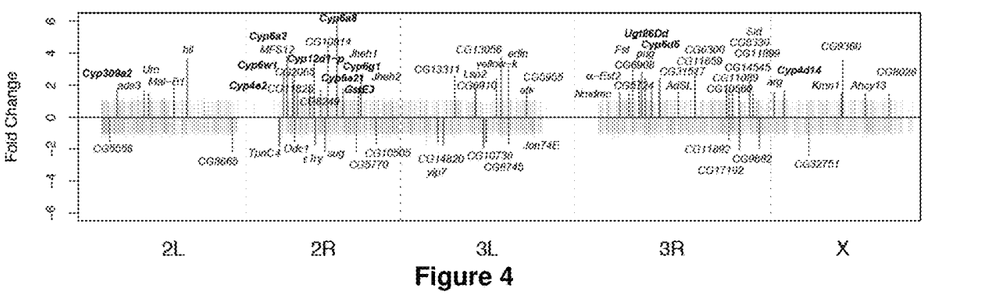
FIG. 4 shows the host's genome-wide transcription response to chronic pesticide exposure (2 mM atrazine).
Figure 5:
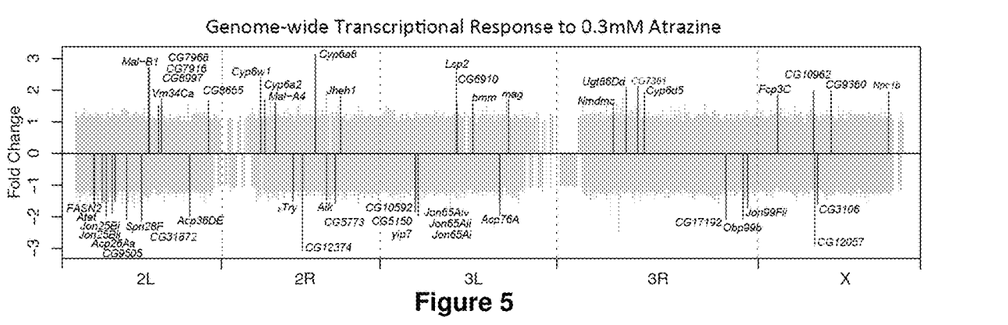
FIG. 5 shows the host response to exposure to pesticide. Atrazine induces an adaptive response associated largely with the transport of lipids, but is not deadly at extremely high doses.
Figure 6:
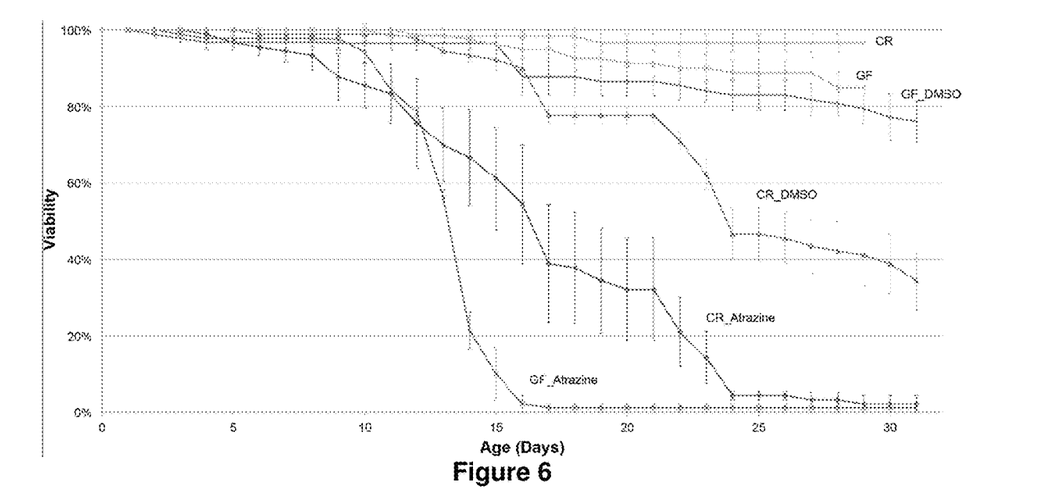
FIG. 6 shows the effect of Atrazine on wild-type and gnotobiotic flies.
Figure 7:
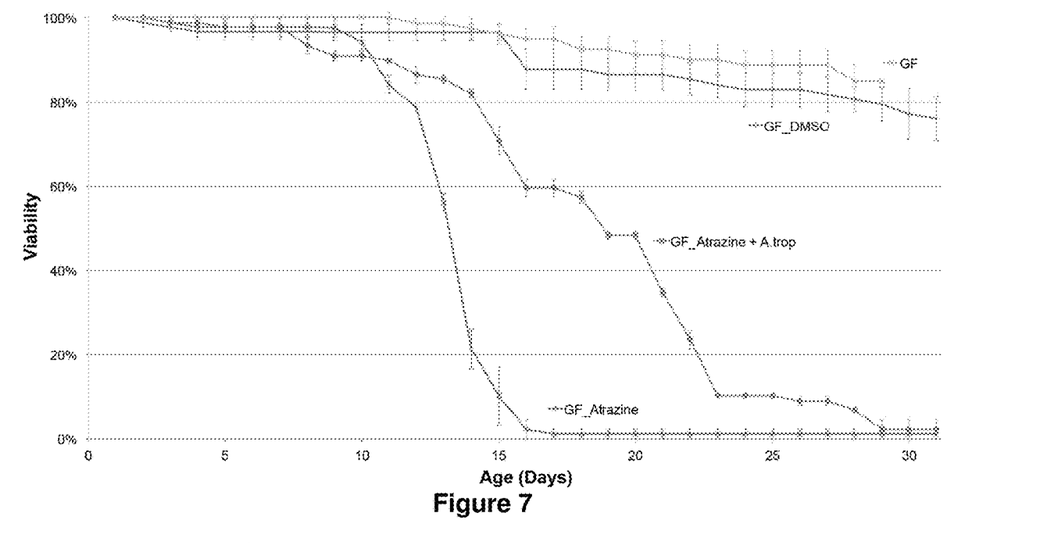
FIG. 7 shows the rescue of Atrazine effects with *Acetobacter.*
Figure 8:
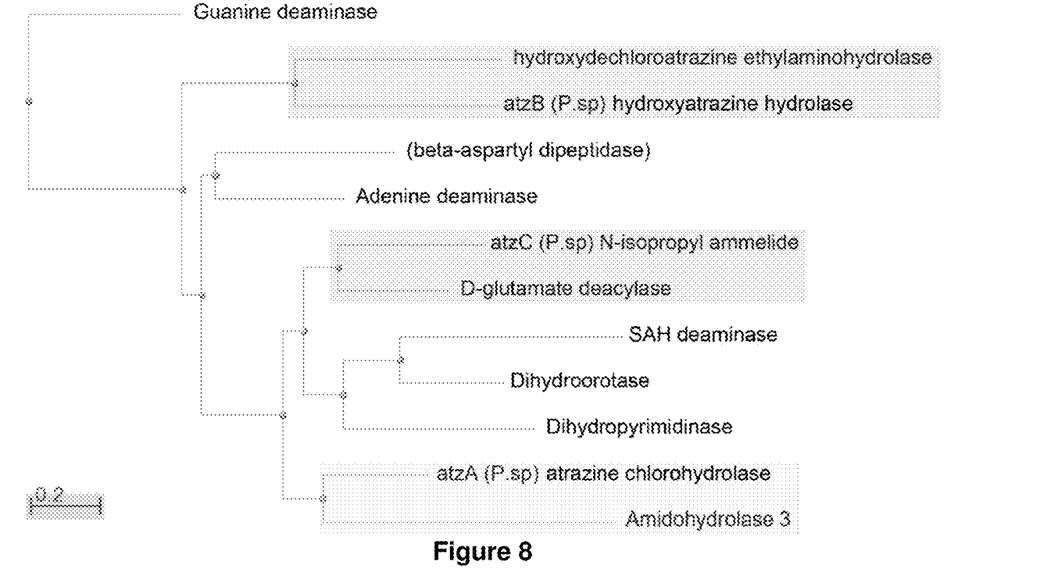
FIG. 8 shows the Amidohydrolase Protein Superfamily and candidate atrazine metabolizing genes from sequenced fly gut microbes.
Figure 9:
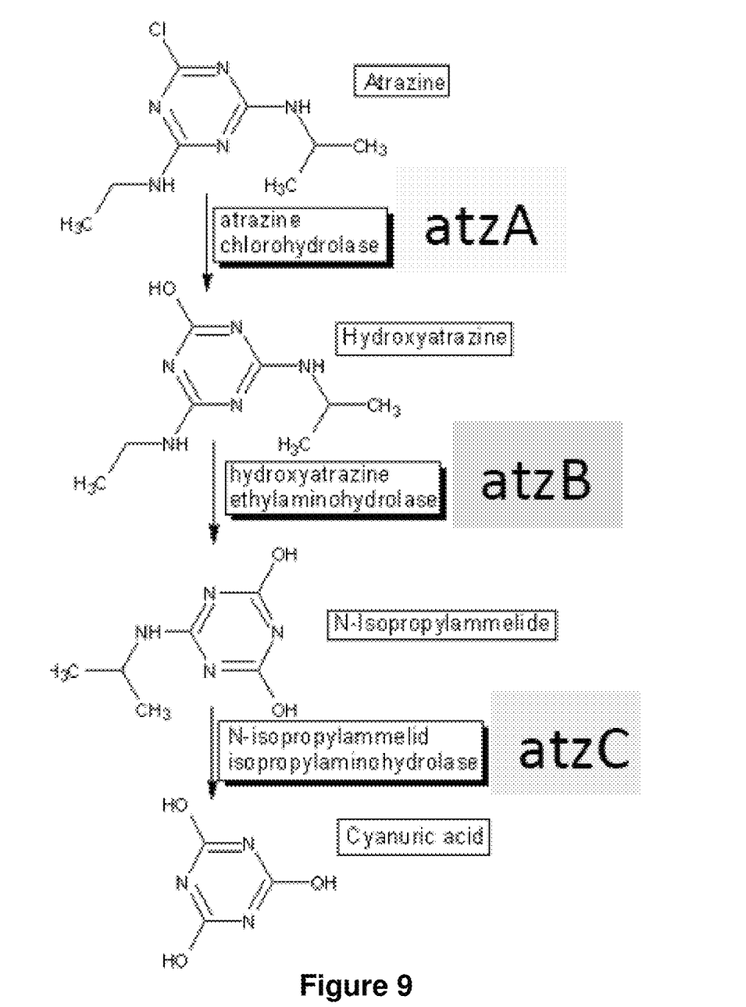
FIG. 9 shows the enzymatic pathway of the Atz enzymes.

Results relating to *Drosophila* are presented in FIGS. 1-9.

REFERENCES CITED

1. Palmer, C., et al., *Development of the human infant intestinal microbiota*. PLoS biology, 2007. 5(7): p. e177.
2. Koenig, J. E., et al., *Succession of microbial consortia in the developing infant gut microbiome*. Proceedings of the National Academy of Sciences of the United States of America, 2011. 108 Suppl 1: p. 4578-85.
3. Dominguez-Bello, M. G., et al., *Delivery mode shapes the acquisition and structure of the initial microbiota across multiple body habitats in newborns*. Proceedings of the National Academy of Sciences of the United States of America, 2010. 107(26): p. 11971-5.
4. Turnbaugh, P. J., et al., *Diet-induced obesity is linked to marked but reversible alterations in the mouse distal gut microbiome*. Cell host & microbe, 2008. 3(4): p. 213-23.
5. Turnbaugh, P. J., et al., *An obesity-associated gut microbiome with increased capacity for energy harvest*. Nature, 2006. 444(7122): p. 1027-31.
6. Ley, R. E., et al., *Microbial ecology: human gut microbes associated with obesity*. Nature, 2006. 444(7122): p. 1022-3.
7. Muegge, B. D., et al., *Diet drives convergence in gut microbiome functions across mammalian phylogeny and within humans*. Science, 2011. 332(6032): p. 970-4.
8. Wu, G. D., et al., *Linking long-term dietary patterns with gut microbial enterotypes*. Science, 2011. 334(6052): p. 105-8.
9. Diaz Heijtz, R., et al., *Normal gut microbiota modulates brain development and behavior*. Proceedings of the National Academy of Sciences of the United States of America, 2011. 108(7): p. 3047-52.
10. Yoshimoto, S., et al., *Obesity-induced gut microbial metabolite promotes liver cancer through senescence secretome*. Nature, 2013. 499(7456): p. 97-101.
11. Caporaso, J. G., et al., *Ultra-high-throughput microbial community analysis on the Illumina HiSeq and MiSeq platforms*. The ISME journal, 2012. 6(8): p. 1621-4.
12. Derrien, T., et al., *The GENCODE v7 catalog of human long noncoding RNAs: analysis of their gene structure, evolution, and expression*. Genome research, 2012. 22(9): p. 1775-89.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A method for enhancing an insect's resistance to a pesticide comprising administering to an insect a probiotic composition comprising: (a) a microorganism capable of expressing one or more enzymes for metabolizing the pesticide, and (b) at least one feed ingredient for an insect.

2. The method of claim 1, wherein the pesticide is an herbicide.

3. The method of claim 2, wherein the herbicide is atrazine.

4. The method of claim 1, wherein the microorganism is an *Acetobacter* species.

5. The method of claim 4, wherein the *Acetobacter* species is *Acetobacter tropicalis*.

6. The method of claim 1, wherein the effective amount of the microorganism is about $1\times10^3$ CFU/g feed ingredient to about $1\times10^{10}$ CFU/g feed ingredient.

7. The method of claim 6, wherein the feed ingredient is white sugar, raw sugar, brown sugar, molasses, and/or waste sugar.

8. The method of claim 1, wherein the composition lacks salt and/or starch.

9. The method of claim 1, wherein the administering step comprises placing the composition in a device configured to attract the insect.

10. The method of claim 9, wherein the device comprises a flower.

11. The method of claim 10, wherein the device comprises a plant comprising the flower.

12. The method of claim 10, wherein the flower is of one species selected from the group consisting of: American Basswood, Southern *Magnolia*, Sourwood, Redbud, Crabapple, Locust, Serviceberry, Tulip Tree, Catmint, Calendula, Bee balm, Sedum, Lavender, Borage, Foxglove, *Crocus*, Anise hyssop, Heliotrope, Pansy, Pussy willow, Siberian squill, Snowdrops, Peony, Milkweed, *Phlox, Zinnia*, Marigold, Goldenrod, Chive, Liatris, Mint, Sage, Nasturtium, Black-eyed Susans, Borage, Thyme, and Oregano.

13. The method of claim 10, wherein the placing step comprises introducing the composition onto the flower, or into a region surrounded by the petals containing the stamen and carpel of the flower.

14. The method of claim 13, wherein the introducing step comprising spraying the composition onto the flower or into the region of the flower.

15. The method of claim 1, wherein the insect is a bee.

16. The method of claim 15, wherein the bee is a honey bee.

17. The method of claim 16, wherein the honey bee of the species *Apis florea, Apis andreniformis, Apis mellifera, Apis cerana, Apis dorsata*, or Apis koschenikovi.

18. The method of claim 1, further comprising the step of mixing a microorganism capable of expressing one or more enzymes for metabolizing the pesticide, and at least one feed ingredient for an insect to produce the composition.

* * * * *